(12) United States Patent
Lambert

(10) Patent No.: US 9,055,756 B2
(45) Date of Patent: Jun. 16, 2015

(54) HEAT EXCHANGE AND TRANSPORT SYSTEM FOR RETORTING APPARATUS

(75) Inventor: David Lambert, Swansea (GB)

(73) Assignee: Research and Development Systems Limited, Swansea (GB)

( * ) Notice: Subject to any disclaimer, the term of this patent is extended or adjusted under 35 U.S.C. 154(b) by 537 days.

(21) Appl. No.: 13/120,995

(22) PCT Filed: Sep. 24, 2009

(86) PCT No.: PCT/GB2009/002315
§ 371 (c)(1),
(2), (4) Date: Mar. 25, 2011

(87) PCT Pub. No.: WO2010/035016
PCT Pub. Date: Apr. 1, 2010

(65) Prior Publication Data
US 2011/0180232 A1  Jul. 28, 2011

(30) Foreign Application Priority Data

Sep. 25, 2008 (GB) .................................. 0817602.5
Sep. 26, 2008 (GB) .................................. 0817678.6

(51) Int. Cl.
| | | |
|---|---|---|
| A23L 3/02 | (2006.01) | |
| A23L 3/00 | (2006.01) | |
| A23L 3/12 | (2006.01) | |
| A23L 3/18 | (2006.01) | |
| B65B 55/14 | (2006.01) | |
| A61L 2/07 | (2006.01) | |

(52) U.S. Cl.
CPC .................. *A23L 3/025* (2013.01); *A23L 3/001* (2013.01); *A23L 3/12* (2013.01); *A23L 3/18* (2013.01); *A61L 2/07* (2013.01); *B65B 55/14* (2013.01)

(58) Field of Classification Search
USPC ........... 99/330, 539, 359, 360, 371, 403–404, 99/409, 467, 470, 366–368; 422/26, 291, 422/305, 292, 298–299; 426/407, 405, 412, 426/232, 511, 512
See application file for complete search history.

(56) References Cited

U.S. PATENT DOCUMENTS

| | | | | |
|---|---|---|---|---|
| 3,511,168 | A | * | 5/1970 | Pech ................................ 99/360 |
| 3,927,976 | A | * | 12/1975 | Reimers et al. ................ 422/296 |
| 4,003,302 | A | * | 1/1977 | Mencacci et al. ................ 99/359 |
| 4,646,629 | A | * | 3/1987 | Creed et al. .................... 99/468 |
| 5,476,635 | A | * | 12/1995 | Stoker ............................. 422/26 |

FOREIGN PATENT DOCUMENTS

| | | | | |
|---|---|---|---|---|
| JP | 2000069948 | A | * | 3/2000 ............... A23L 3/10 |
| JP | 2008043781 | A | * | 2/2008 |

* cited by examiner

*Primary Examiner* — Jianying Atkisson
(74) *Attorney, Agent, or Firm* — Galgano & Associates, PLLC; Thomas M. Galgano; Jessica G. Bower

(57) ABSTRACT

An apparatus for the heat treatment of a product, in particular a product contained within a hermetically sealed pouch or other plastic container, the apparatus having, a heating unit to contain a product as product is brought towards a treatment temperature and pressure, a sterilization unit to contain product at a pre determined treatment temperature and pressure to sterilize product, and a cooling unit to bring a product from the treatment temperature and pressure towards ambient; each unit being selectively sealable from another unit, the apparatus further having: a plurality of conduits carrying heat-exchange fluids allowing heat to be transferred between units; and having a heater, preferably producing steam, to supply heat to the apparatus; a heat-exchange unit enabling heat energy to be transferred from one conduit to another; and a hot well to retain a reservoir of heat exchange fluid at the highest temperature required by the apparatus.

17 Claims, 5 Drawing Sheets

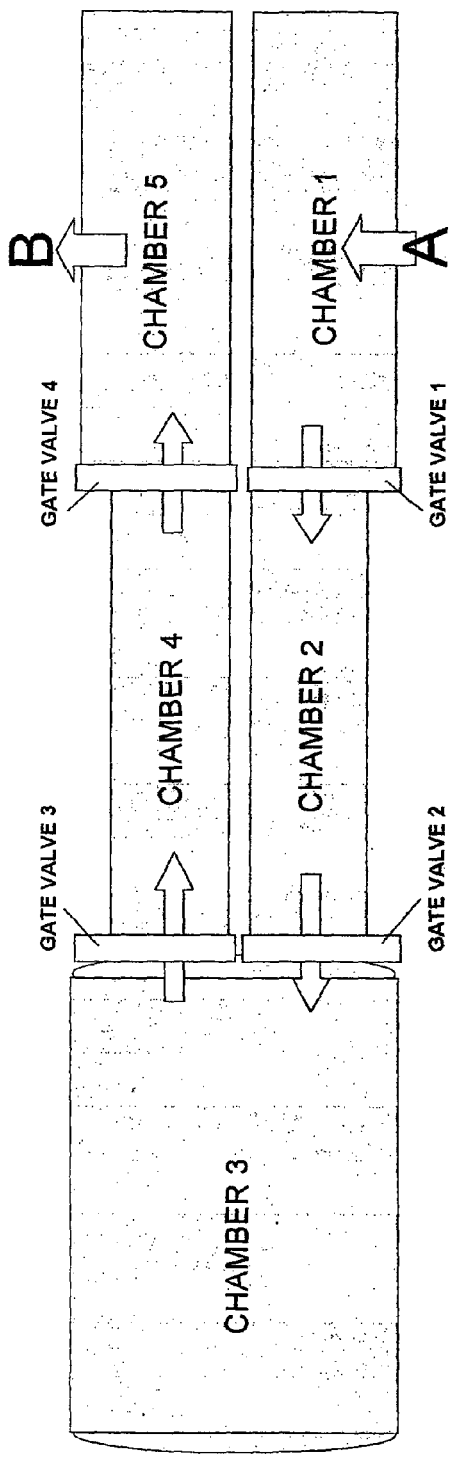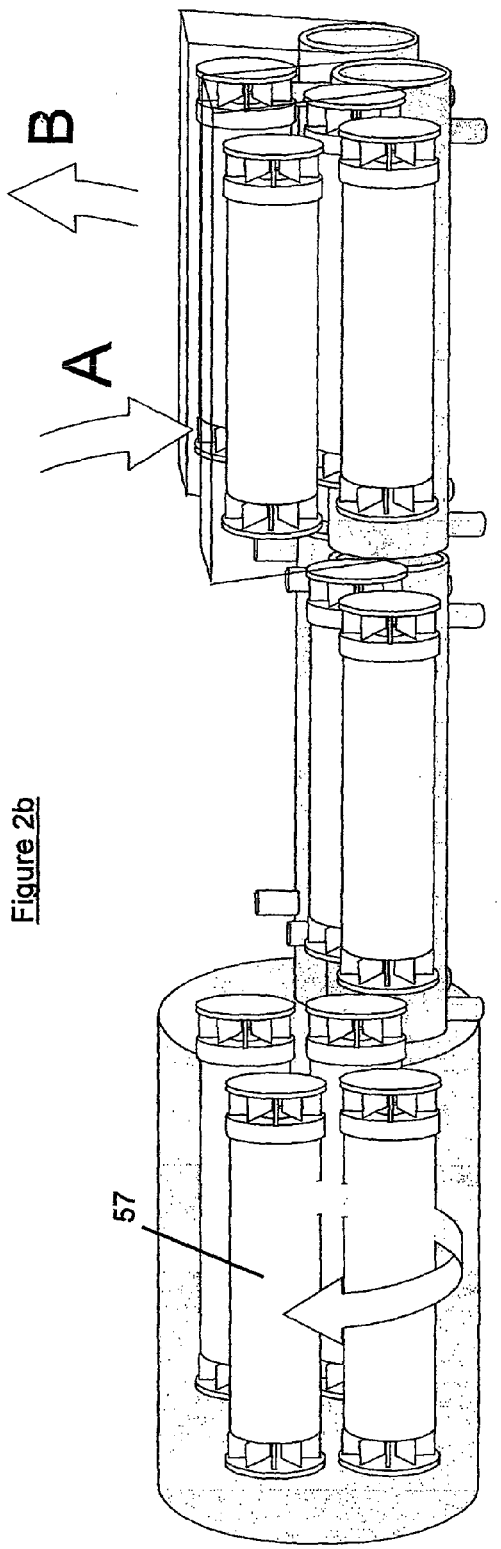

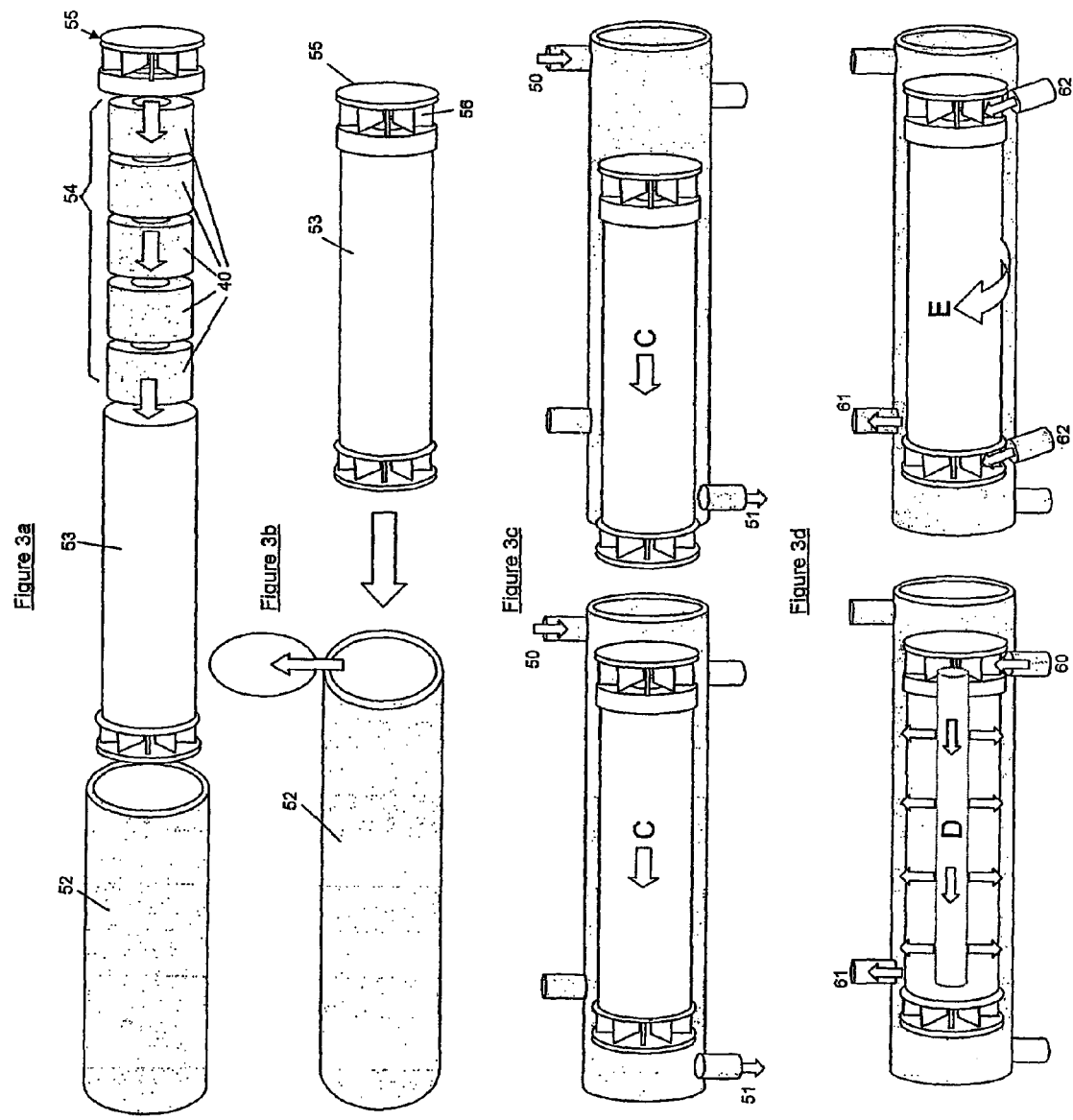

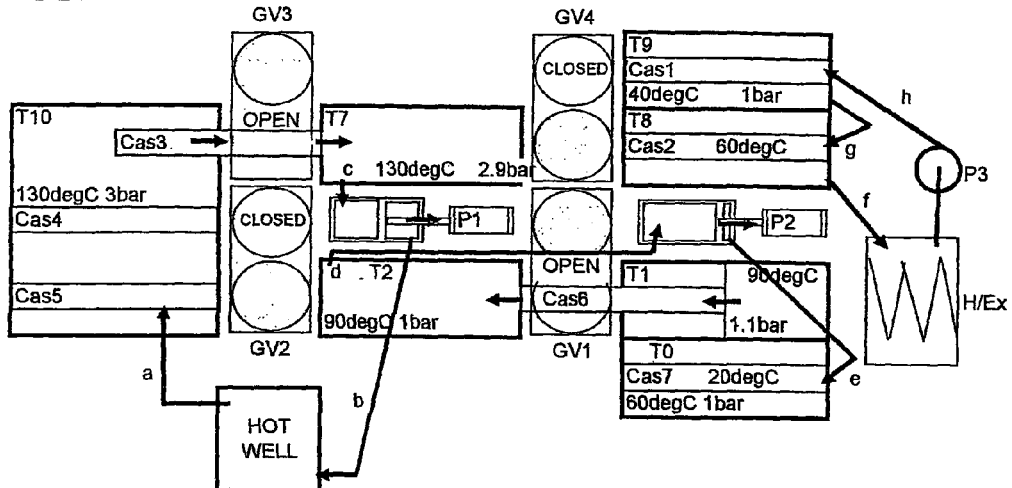
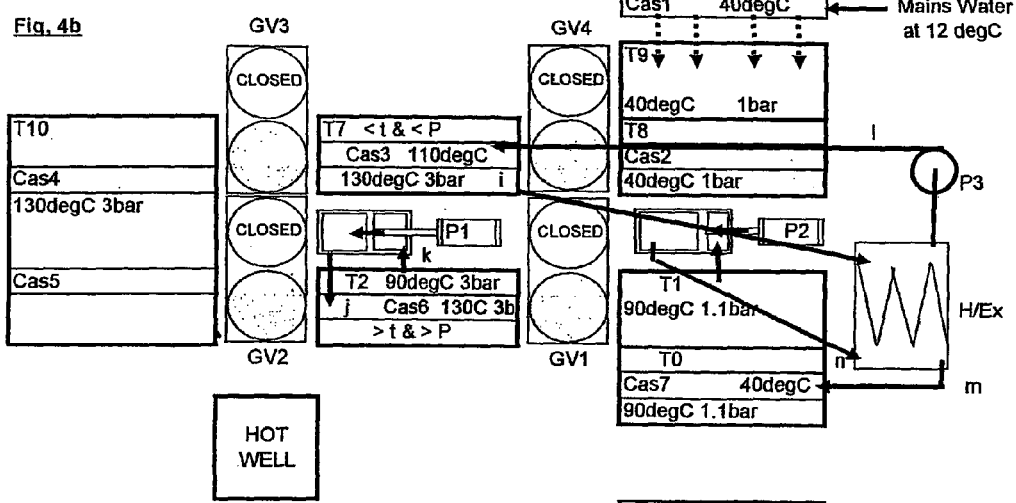
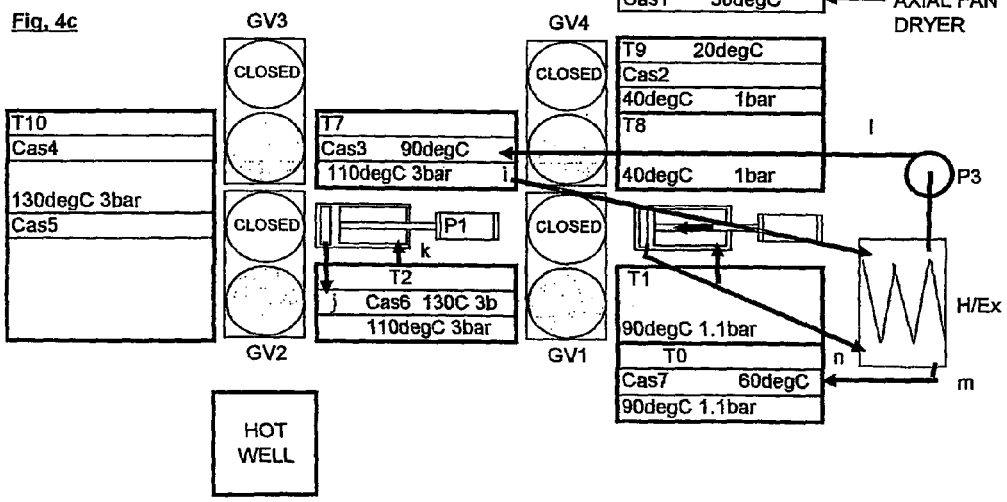

HEAT EXCHANGE AND TRANSPORT SYSTEM FOR RETORTING APPARATUS

FIELD OF THE INVENTION

The present invention is concerned with a retorting apparatus used in the heat treatment of food products and in particular with a heat exchange system incorporated therein.

BACKGROUND TO THE INVENTION

The heat exchange system as herein described is useful in conjunction with any continuous retorting apparatus in order to control the particular heat transfer fluids used within that apparatus. Nevertheless, the system is especially suited and described with reference to the retorting apparatus described in International (PCT) Patent Application No. PCT/GB08/01146. In order to improve the functioning of a retorting apparatus, the invention described in PCT/GB08/01146 utilises a plurality of enclosed volumes, each separately sealable from other volumes, the product moving serially from one volume to another.

With increasing energy prices and also a desire to reduce so-called greenhouse emissions, minimising energy wastage is increasingly important. Prior art batch retorts are not on the whole energy efficient, and the ineffective usage of the energy in the heating fluids results in a large amount of energy and water being wasted.

Continuous retorts can be significantly more energy efficient, but have failed to become commercially acceptable due principally to excessive complexity, size and cost compared to existing batch retorts.

The present invention therefore seeks to address the above problems and produce a retorting apparatus incorporating a heat exchange system which provides optimised energy usage as well as providing the means of transporting the product through the retort, thereby significantly reducing the complexity and cost of the retort.

SUMMARY OF THE INVENTION

According to a first aspect of the invention there is provided an apparatus for the heat treatment of a product, in particular a product contained within a hermetically sealed pouch or other plastic container, the apparatus comprising, a heating unit to contain a product as product is brought towards a treatment temperature and pressure, a sterilisation unit to contain product at a predetermined treatment temperature and pressure to sterilise product, and a cooling unit to bring a product from said treatment temperature and pressure towards ambient;

each unit being selectively sealable from another unit, the apparatus further comprising:

a plurality of conduits carrying heat-exchange fluids allowing heat to be transferred between units;

and comprising a heater, preferably producing steam, to supply heat to the apparatus;

a heat-exchange unit enabling heat energy to be transferred from one conduit to another;

a hot well to retain a reservoir of heat exchange fluid at the highest temperature required by the apparatus.

Preferably the apparatus comprises a plurality of heating units, enabling the heating to be carried out in staged steps and increasing the efficiency of energy usage.

Optionally, the heat-exchange unit includes a heat pump.

The apparatus preferably includes a plurality of cooling units enabling the cooling to be carried out in staged steps, and again increasing the efficiency of energy usage.

Preferably, the hot well retains water at a temperature of greater than 110 C and further preferably below 130 C.

Conveniently the apparatus includes a magazine to retain a product combining pouch convey a product containing pouch through the apparatus. Further conveniently the magazine is rotably mounted about a central shaft, said shaft being so configured to receive a plurality of magazines.

Preferably, heat is conveyed through the apparatus by a liquid. Further preferably, the fluid acts to exert a force on product to facilitate motion of product through the apparatus. The shaft and magazines are advantageously surrounded by a casing, further advantageously of tubular construction to allow easier handling of product. The casing optionally has one or more apertures in the wall of the casing to enable fluid to circulate within the casing and about the product. Advantageously, the casing includes pins or baffles on the outer surface to increase the force felt by the casing due to flow of heating fluid.

Preferably excess water in excess of that needed by the retort is returned to the heat well. Further preferably, a valve is included preventing flow of water having a temperature of greater than 125 C into the hot well.

The apparatus preferably includes one or more fans to draw air through a unit to aid heat transfer.

BRIEF DESCRIPTION OF THE DRAWINGS

The invention will now be described with reference to the accompanying drawings which show by way of example only, two embodiments of a retorting apparatus and heat exchange system. In the drawings:

FIGS. 2a and 2b are diagrammatic illustrations of product-containing cassettes secured within magazines passing through the apparatus; and FIGS. 3a-3d illustrate passage of cassettes into a heating chamber as well as details of heat transfer fluid flows and hydraulic rotation.

FIGS. 4a-4f are diagrammatic illustrations of the same retort without the heat pump but utilising a simple heat exchanger instead and showing the various stages of heat exchange and hydraulic transfer along with the associated conduits;

DETAILED DESCRIPTION OF THE INVENTION

Figure 1:
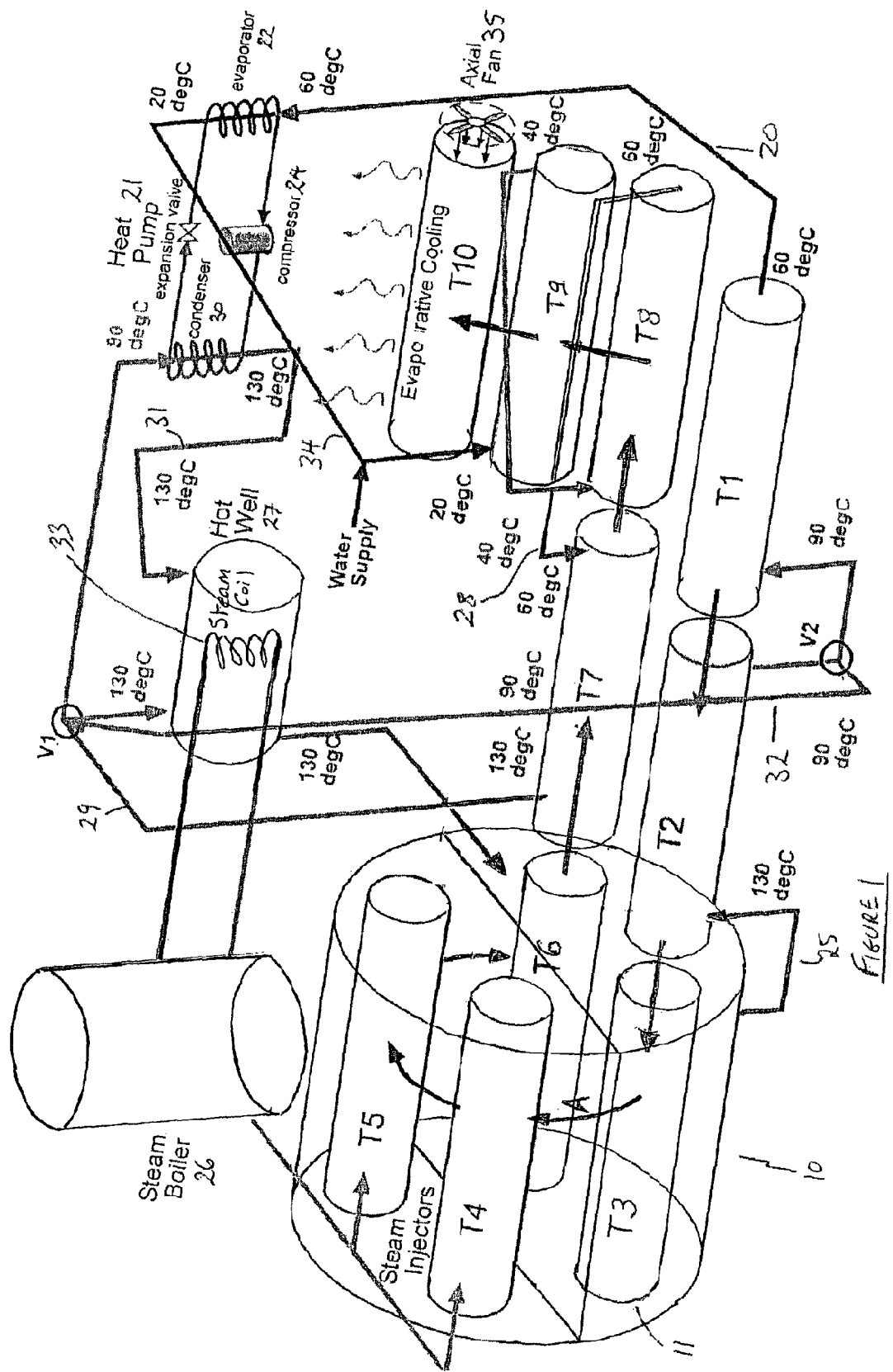
FIG. 1 is a diagrammatic illustration of a retort and heat exchange system incorporating a heat pump.

The retorting apparatus as shown in FIG. 1 is suitable for sterilising food products retained within a sealed container and particularly suitable where the container is formed of a plastics material.

The product being processed through the apparatus is subjected to a heating and a pressurising cycle in which the product is brought from ambient conditions to elevated temperature and pressure conditions to accomplish sterilisation before being returned to ambient.

In general, the system for controlling the temperature and pressure comprises a heat source in the form of a boiler, which provides steam directly to a number of elements of the system. A heat exchanger enables energy to be transferred from one fluid conduit to be transferred to another without the risk of bacterial contamination being passed over. In addition a heat pump provides energy savings by enabling partially cooled water to be cooled to ambient and distributing the energy removed from that water to another volume of water which requires heating. A hot well, including a supply of steam heating direct from the boiler, is also provided to deal with the handling of water at the hottest temperatures used by the system, above 110 C, and the heating and storage of such water at the maximum required at around 130 C.

By providing for energy to be movable between areas of energy deficit and surplus, the energy efficiency of the retort apparatus is improved.

Referring in detail to the embodiment shown in FIG. 1, this shows a retorting apparatus in which batches of food product held within a container are progressively heated and then cooled, prior to being packaged for sale. The product is typically mounted in a magazine which then passes from one chamber (labelled T1, T2 and T7-T10) to the next. Within the main sterilisation chamber 10 the magazine is mounted on a housing for rotation about the central axis of the retort between positions T3-T6. Whilst undergoing this larger scale rotation of movement, the magazine can also rotate relative to the housing thereby increasing the overall rotation to ensure even heating of product, or improved ingredient mixing, or improved internal heat transfer. Alternatively, the magazine can be counter rotated to eliminate or reduce such rotation where this is of benefit to the product, such as in products where compaction can reduce quality.

In FIG. 1, chamber T1 is used to load magazines or cassettes of product containers into a position from which they can be carried through the continuous retort and within which initial heating can commence by direct contact heat transfer from hot water at approximately 60 C circulating within. The magazines in chamber T1 can be rotated by the support shafts, or by the hydraulic action of pressurised water impinging upon fins attached to the magazines to allow any trapped air to be evacuated by gravitational displacement and to permit mixing of ingredients if needed.

Once the first chamber contains the required number of magazines the gate valve connecting chambers T1 and T2 is opened so that the magazine full of cassettes can be transported by the drive chain located between the two rotational shafts, or by the hydraulic action of heat transfer fluids being sucked from T1 into the primary heating chamber T2.

The chamber T2 is sealed by the closure of this gate valve and the 90 C water contained therein is replaced by hotter pressurised water over a period of minutes to take the product up to the final sterilisation temperature and overpressure. The magazines in chamber T2 can also be rotated by mechanical or hydraulic means to allow further mixing of ingredients if needed. After the required time the gate valveconnecting T2 with chamber 10 is opened so that the magazines can be transported by either mechanical or hydraulic means into the chamber 10

The main chamber 10 comprises a main substantially cylindrical pressure vessel. During operation of the chamber 10, a body of water 11 is maintained at such a level that the product passes therethrough. Within the main chamber 10 is disposed a large rotational frame holding four tubular compartments into which the product container magazines are loaded. It should be evident to the skilled observer that the number of tubular compartments fitted into the chamber 10 is chosen to suit the user and expected product. The tube can have a central spargepipe along its length enabling heating fluid to flow along its length, or alternatively the hollow centres of each cassette can act collectively as a sparge pipe.

The chamber 10 is kept at the required sterilisation temperature and pressure by the introduction of steam at a pressure of 5 bar via the two upper sparge pipes which are above the water level. If necessary compressed air can also be used to augment or help the control of overpressure. The temperature and pressure are maintained at these constant values during a full normal period of operation of the retort, which could easily be several days in duration.

Loading of magazines into the chamber 10 from the chamber T2 takes place such that the magazines enter the lower half of the chamber 10 below the water level maintained within the chamber 10. After a preset time within the pressurised water a magazine, is rotated upwardly, in the direction indicated by the arrow A between positions T3 and T6, out of the water (indicated by the shaded region 11) and into the pressurised steam above the water surface. Alternatively, the entire chamber 10 may be flooded with pressurised water.

Independent rotational means are provided, either mechanical or hydraulic, to provide additional rotation of product at positions T3-T6 or to counter rotate to eliminate the effect of the rotation of the magazine carrier or to provide pre programmed rotation or counter rotation as required.

Before unloading from T6 can commence the first cooling chamber T7 needs to be filled with high temperature water and pressurised to sterilisation over pressure by closing its gate valves and transferring its contents to T2 to heat the incoming product at the same time as filling it from the chamber 10. The water pumped from chamber 10 is made up from the hot well.

As soon as the pressures and temperatures are equal in both chamber 10 and T7 the interconnecting gate valve can be opened. Once the gate valve is fully open the product magazine in position T6 is transferred to the chamber 17 by either mechanical or hydraulic means.

When the chamber T7 has received its product magazine, the gate valve closes and the high temperature water is pumped back into the lower section of the baffled hot well 27 and replaced with water from T8 at around 60 C, thereby cooling the product to around 90 C.

The chamber T8 is the location of the second stage of cooling where the product is cooled from 90 C to 60 C by pumping in water at 40 C from the chamber T9.

From the chamber T8, the product then passes into two further chambers T9, T10 in which it is further cooled to 40 C and 30 C respectively. In the final chamber T10 a fan 35, axially located with respect to the chamber T10 dries and cools the product by evaporative cooling of the water on the outside of the product containers.

Dealing now with the heating and cooling system in more detail, unprocessed product enters the chamber T1. Water from the chamber T2 which is at a temperature of around 90 C is pumped, via the valve V2, into the chamber T1. This preheats the product to around 80 C. In doing so, the energy lost to the product causes the temperature of the water to fall to around 60 C. This cooler water is pumped via a conduit 20 to a heat exchanger, which in the described embodiment comprises a heat pump 21, and in particular to the evaporator 22 of the heat pump 21. Here the water is cooled to 20 C by means of a refrigerant contained within a coil 23 of the evaporator 22. The energy now held in the refrigerant is passed via a compressor 24 to a heating section (see below) of the heat pump 21. The chilled water is either returned directly to the chamber T9 via conduit 34 or is circulated through a heat exchanger (not shown) to keep segregation of product cooled heating water (which may be contaminated) from the heat treated product which is being cooled.

The product, when at a temperature of around 80 C passes to the chamber T2. Here, water from the chamber retort 10, at a temperature of around 130 C passes by the conduit 25 to the chamber T2. Energy from the water is used to heat the product. In doing so, the temperature of the product is raised to around 125 C and the temperature of the water falls to around 90 C, ready to be pumped into T1 as described above. The product then passes into the retort 10 at position T3. The water 11 is at a temperature of 130 C and is maintained in liquid form by the pressure within the retort 10. The temperature of the water 11 acts to commence sterilisation of the product. Part or all of the loss of heat energy of the water 11 occasioned by this step is replaced by that from the steam above the water level.

The temperature within the retort 10 is maintained at 130 C by heat from two sources. Firstly, steam is obtained directly from the boiler 26. Secondly, heated recycled water is obtained from the hot well 27.

Once the sterilisation process is complete, product passes from the retort 10 to the chamber T7 where the product is cooled by water having a temperature of around 60 C and obtained from the chamber T8 via the conduit 28. The product temperature therefore falls from 130 C to around 90 C. The water, before cooling, passes via a conduit 29 and the valve V1 to the hot well 27 to be heated to 130 C ready for re-use to heat the chamber 10.

Initially, when the product is at a 130 C having just exited the chamber 10, the water flowing along the conduit 29 is above 125 C and the valve V1 directs the water directly into the hot well 27. As the temperature of the product falls however, the water temperature in the conduit 29 also falls. Below a temperature of 125 C, the valve V1 directs the water to the condenser 30 of the heat pump 31. Here heat is removed from the refrigerant bringing the water to around 130 C, which water than passes via a conduit 31 to the hot well 27. It should be noted that whilst the water from the conduit 29 is being passed by the valve V1 directly into the hot well 27, water at around 90 C is drawn via a conduit 32 from the chamber T2 into the condenser 30. When required, water in the hot well 27 can be heated by heat taken from the steam drawn from the steam boiler 26 by means of a coil 33. Alternatively, in applications using heat pumps with refrigerant fluids which are more suited to lower temperatures, the heat pump is used mainly to augment efficient heat transfer from the cooling water and the steam boiler is the only means to add heat energy to the medium to high temperature water in the 65 to 90 C range which is then heated to 130 degrees C.

The product in the chamber T7, once it has reached a temperature of around 90 C is transferred to the chamber T8, where further cooling to around 60 C takes place. The cooling is achieved by pumping water from the chamber T9, the water having a temperature of around 40 C into the chamber T8. Similarly, on passage to the chamber T9, the product is cooled to a temperature of around 40 C. In order to achieve this, cooling water from the evaporator 22 at a temperature of around 20 C, is pumped via a conduit 34, or via the segregating heat exchanger, into the chamber T9. Finally, the product is transferred from the chamber T9 to the chamber T10 where the product is dried, through evaporative cooling by air drawn through the chamber T10 by the axially oriented fan 35 mounted thereto. Water losses are made up by running water from a potable mains supply via a break tank into the chamber T9 to the required level.

Turning now to FIGS. 2, 3 and 4, a further feature of the apparatus is hereby exemplified. The movement of the product-bearing magazines is illustrated in simplified form in FIGS. 2a and b. In summary, the product containing magazines 57 are loaded into the apparatus at location A. They then pass through a series of chambers in the direction shown by the arrows before exiting the apparatus at position B. The chambers are shown in FIG. 2a as being five in number, although it will be recognised that this number can be chosen to suit the intended application. The chambers 1-5 are separated from one another by a series of gate valves 1-4 which can isolate chambers from each other when closed.

The heating and heat exchange system described above assists in movement of product between chambers, as exemplified in FIGS. 3a-3d. The entry and exit points 60 and 61 are so located that heating or cooling fluid flows through a chamber 52 in the direction of movement of the magazines 57 which contain cassettes 40 which bear product. The magazines 57 retain the cassettes 40 by means of end caps 55 which are of larger diameter than the magazines 57. When the magazine 57 has to be moved within the retort the pressure in conduit 60 in increased relative to that in conduit 61 by a pump. The force generated by differential pressure on the end caps 55 thereby causes the magazines to move in the required direction. The efficiency of this process along with the product treatment process in general, is improved through the segregation of 'slugs' of water which can be at different temperatures in 60 and 61 and are effectively kept from mixing by the end caps. This is particularly useful where the next set of conditions in the newly vacated chamber are designed to be different to those being used prior to the transfer of the magazine out of the chamber.

The tubular magazine arrangement 57 comprises a cylindrical portion 53 into which an array of five product carrying cassettes 40 is passed. The cylinder 53 includes perforations which enable heating fluid to freely circulate within and pass through the cylinder 53 to heat or cool product.

Once the product is located within the cylinder 53, end plates 55 are secured over the ends of the cylinder 53 and the complete magazine 57 is loaded into the chamber 51. The pressure in chamber 51 is now increased relative to that in chamber 52. When the gate valve 58 on the exit end of chamber 51 is opened, the magazine containing the product is moved into the next chamber 52 in the direction shown by Arrow C in FIG. 3b by the pressure differential now acting on the end caps 55 which in turn produces a translational force.

FIG. 3c shows that this transfer of magazines can be actuated from within a single chamber by flow from 60 to 61 as described above.

The energy efficiency of the apparatus is thereby increased as the heat exchange fluid doubles as the motive force fluid. Moreover, the requirement for additional mechanical features to cause this motion is also reduced.

It will be appreciated that although the end plate of 55 must be solid the other elements of the end cap can be open and can include features to improve engagement and force exerted on the cylinder 53 by the fluid flow. Moreover, the end cap can also include features such as fins 56 or baffles to increase or redirect the said force, distribute heat exchange fluids more efficiently, or enable rotation or counter rotation of the cylinder.

FIG. 3d shows two such features. When heat transfer fluids are directed via conduit 62 they enter the end cap between two end plates, the inner one of which has an open centre which aligns with the hollow core of the product bearing cassettes which directs the fluid into the said core in the direction of arrow D. As the outlet 63 is inboard of the other end cap it can only accept fluids which have been forced between the individual product pouches or containers in an outwardly radial flow as shown by the eight smaller arrows. Of course this flow is in fact taking place over 360 degrees, not just in one plane as shown here. The second drawing shows the effect of adding an extra inlet and canting them now shown as 64. The inlet fluids now impinge on the fins 56 and cause a rotational effect in the direction of arrow E. It can therefore be seen that the retort designer now has multiple options to make use of the heat transfer fluids in the detailed management of the product as it passes through each stage of the continuous retort.

FIGS. 4 a-f shows the same retort as FIG. 1 but with different pipework to permit hydraulic transfer of product magazines or 'cassettes' and shows the progression of cassettes 1 to 8 passing through that retort. The four stages of loading, heating, cooling and unloading are managed in this embodiment alongside the flow of heat transfer fluids for both heat transfer as well as physical transfer of cassettes.

FIG. 4a shows stage 1 with gate valves GV1 and GV3 open. The cassette 3 (Cas3) is being transferred from the chamber T10 to the chamber T7 by the pumping of 130 C water from chamber T7 to the inlet chamber of piston pump P1 via conduit c. At the same time the discharge side of the piston pump P1 is transferring water at 130 C to the hot well via conduit b. The water entering the hotwell at the lower section displaces water from the top section back into chamber T10 via conduit a. All of these transfers are taking place from a base pressure of 3 bar with the pumping action of P1 providing sufficient over/under pressure to ensure hydraulic force sufficient to provide the necessary transfer of the two cassettes being moved.

At the same time the cassette Cas6 is being transferred from chamber T1 to chamber T2 by the action of the piston pump P2 which is sucking water at 90 C from the chamber T10 side of the chamber T2 via conduit d and at the same time is pumping water at 90 C through a conduit e into the newly loaded cassette 7 via its hollow central core, thereby increasing the head in both chambers T0 and T1 which completes the hydraulic circuit and forces the cassette 6 to move into chamber T2.

FIG. 4b shows the beginning of stage 2. All four gate valves are now closed and piston pump P2 is now on its return stroke pumping water at 90 C from its new discharge side (which had been taken from chamber T2 in stage 1) into the core of the cassette 7 via conduits n and m and the un-sterilised water side of heat exchanger x, thereby further heating the product within the cassette 7. This water is being heated in the heat exchanger by hot water on the sterilised water side which is being circulated by centrifugal pump P3 via conduits i and l through the core of cassette 3 within chamber T7, thereby cooling the product contained in cassette 3.

Product in cassette 6 is being heated from 90 C to over 110 C and around 2.2 bar by the action of both the discharge and inlet sides of piston pump P1 via conduits j and k.

Cassette 1 is being withdrawn from chamber T9 and mains water is introduced to the core of cassette 1 to further cool the product contained therein from 40 C to 30 C. The excess water drains into chamber T9 by gravity, cooling the water in chamber T9 to between 20 C and 40 C.

FIG. 4c shows the end of stage 2, some two minutes after its start. The product in the cassette 7 is now around 60 C, an increase of 40 C from ambient and that in cassette 3 is now around 90 C, 40 C lower than sterilisation temperature. The temperature of product in the cassette 6 is now at almost 130 C and the pressure in chamber T2 has been increased to 3 bar.

The final cooling and drying of cassette 1 and its product is achieved by forced air from the axial fan through its core.

Figure 4D:
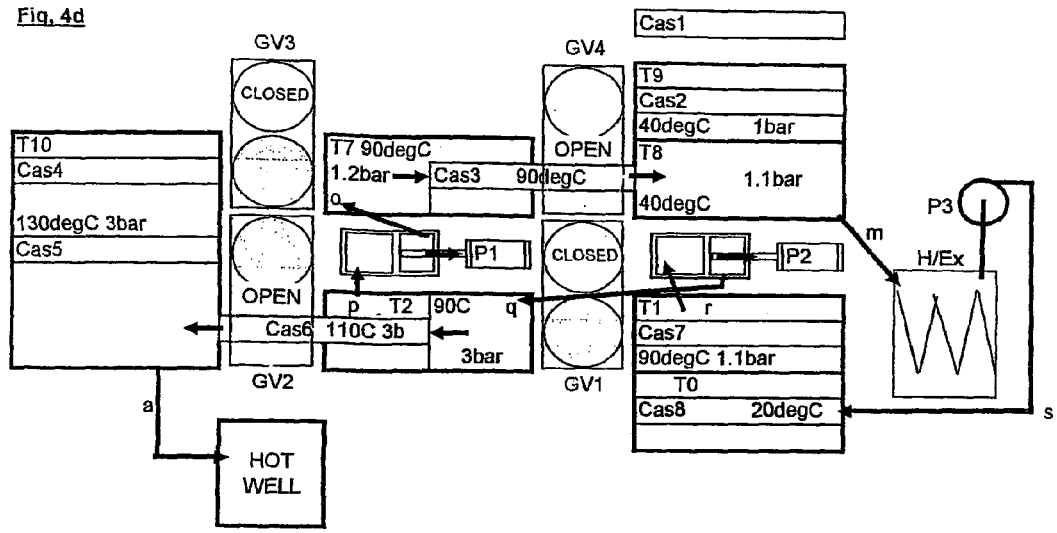

FIG. 4d shows stage 3. The pressures in T7 and T6 are now equalised enabling the gate valve GV4 to open and cassette 3 to be transferred by the hydraulic action of water being pumped from the discharge side of piston pump P1 at 1.2 bar against the lower pressure head of 1.1 bar in chamber T8. The water flow into chamber T8 is drawn into the suction side of centrifugal pump P3 via conduit m and the heat exchanger x and thence via conduit s into the core of the newly loaded cassette 8 which is at 20 C.

Figure 4E:
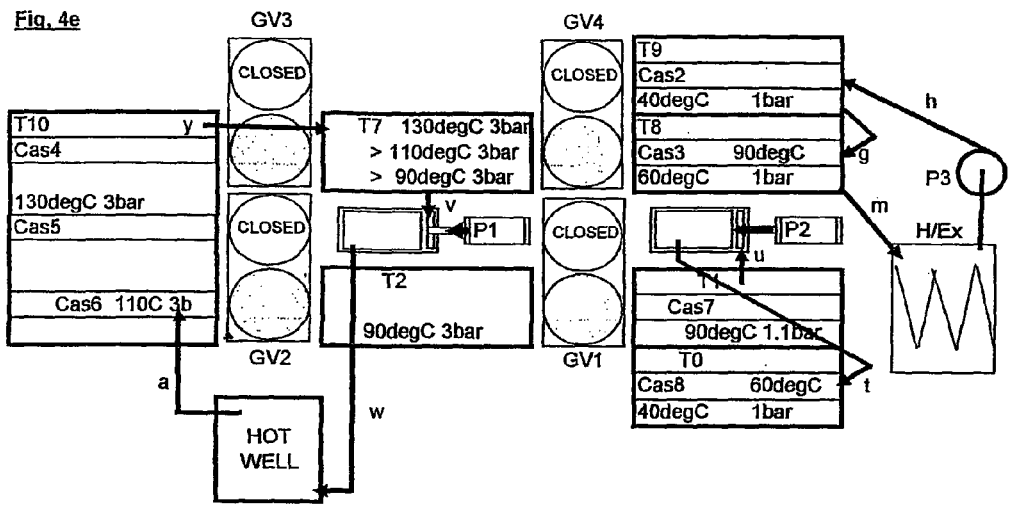

The pressures in chambers T10 and T2 are also equal at 3 bar enabling gate valve GV2 to open and the hydraulic action of water at 90 C and 3 bar being pumped from P2 via conduit q to the chamber T0 side of chamber T2 to transfer cassette 6 into chamber T10. Overflow water at 130 C from chamber T10 is returned to the hotwell via conduit a. The cassette 1 is now ready for removal from the retort. FIG. 4e shows the start of stage 4. All gate valves are again closed. The chamber T7 is pressurised from 1.2 bar up to 3 bar by the opening of conduit y which then allows the transfer of water at 130 C into chamber T7, mixing with the water at 90 C contained within chamber 17 which in turn is drawn into the inlet side of piston pump P1 via conduit v at an aggregate temperature of 110 C.

The water contained in chambers T9 and T8 is circulated through the heat exchanger and cassettes 2 and 3 via conduits h, g and m by piston pump P3 until the temperature in conduit h exceeds that in T9.

The 90 C water in the discharge side of piston pump P2 is pumped into the core of cassette 8 to heat it from 60 C. Excess water at 90 C is drawn into the inlet side of piston pump P2 from chamber T1.

The 110 C water in the discharge side of piston pump P1 is pumped into the base of the hot well where it is heated to 130 C by the boiler (not shown). Mixing of water at 110 C and 130 C is avoided through the use of baffles within the hot well. Water at 130 C is thereby pumped via conduit a into the core of cassette 6 within chamber T10, heating the product contained therein from 110 C to 130 C.

Figure 4F:
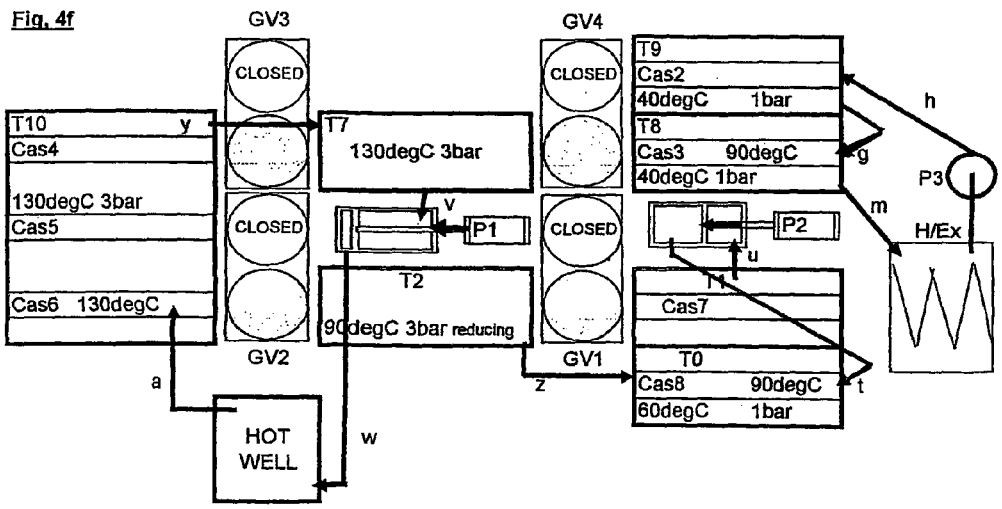

FIG. 4f is the end of stage 4. Chambers T0, T1 and T2 are all now at 90 C. The excess pressure in chamber T2 is bled into chamber T0 via the core of cassette 8 via conduit z. The cycle of 4 stages is now ready to be repeated.

It will of course be understood that the invention is not limited to the specific details described herein, which are given by way of example only, and that various modifications and alterations are possible within the scope of the invention.

The invention claimed is:
1. An apparatus for the heat treatment of a product, the product being contained within a plastic container, said apparatus comprising:
    at least one heating unit to heat the product contained therein, towards a pre-determined treatment temperature and pressure, said at least one heating unit having means for adjusting the temperature and pressure therein;
    a separate sterilization unit having a chamber, said sterilization unit connected in series with said at least one heating unit to permit the product to be transferred from said at least one heating unit to said sterilization unit, said sterilization unit to sterilize the product contained therein at a pre-determined treatment temperature and pressure and having means for adjusting the temperature and pressure therein; and
    at least one separate cooling unit connected in series with said sterilization unit to permit the product to be transferred from said sterilization unit to said at least one cooling unit, said at least one cooling unit to cool the product contained therein from said pre-determined treatment temperature and pressure towards ambient and having means for adjusting the temperature and pressure therein;

wherein each of said units comprise means for selectively sealing said unit from said adjacent units, and all of said units are capable of running simultaneously;

a plurality of conduits connected to said units, said conduits carrying heat-exchange fluids, and being arranged to allow heat to be transferred between units;

a heater producing steam coupled to said apparatus to supply heat to said apparatus;

at least one heat-exchange chamber configured to allow heat energy to be transferred from at least one of said conduits to at least another of said conduits; and a hot well coupled to said apparatus to retain a reservoir of heat exchange fluid at the highest temperature required by said apparatus;

and wherein the product is transported in series through said units, and said means for adjusting the temperature and pressure of said units comprises means for equalizing the temperature and pressure of adjacent units before transportation of the product between adjacent units, through the transfer of said heat-exchange fluids into said unit via said conduits and means for varying the temperature and pressure in said unit once the product has been transferred into said unit, through the transfer of said heat-exchange fluids into said unit via said conduits.

2. The apparatus according to claim 1, further comprising:
a plurality of separate heating units, enabling the heating to be carried out in staged steps.

3. The apparatus according to claim 1, wherein:
said at least one heat-exchange chamber includes a heat pump.

4. The apparatus according to claim 1, further comprising:
a plurality of separate cooling units enabling the cooling to be carried out in staged steps.

5. The apparatus according to claim 1, wherein:
said hot well retains water at a temperature greater than 110° C.

6. The apparatus according to claim 5, wherein:
the temperature is maintained below 130° C.

7. The apparatus according to claim 1, further comprising:
at least one magazine to retain the product and convey the product through said apparatus.

8. The apparatus according to claim 7, wherein:
said at least one magazine is rotatably mounted about a central shaft, said shaft being so configured to receive a plurality of magazines.

9. The apparatus according to claim 1, wherein:
heat is conveyed through said apparatus by a liquid.

10. The apparatus according to claim 9, wherein:
fluid acts to exert a force on the product to facilitate motion of the product through said apparatus.

11. The apparatus according to claim 8, wherein:
said shaft and said magazines are surrounded by a casing.

12. The apparatus according to claim 11, wherein:
said casing is of tubular construction.

13. The apparatus according to claim 1, wherein:
excess water in excess of that needed by said apparatus is returned to the heat well.

14. The apparatus according to claim 13, further comprising:
a valve preventing flow of water having a temperature of greater than 125° C. into said hot well.

15. The apparatus according to claim 1, further comprising:
at least one fan to draw air through said at least one cooling unit to dry the product after cooling.

16. The apparatus according to claim 1, wherein:
the plastic container is a hermetically sealed pouch.

17. The apparatus according to claim 7, wherein:
a fluid acts to exert a force on the product to facilitate rotation of the product within said at least one magazine.

* * * * *